(12) United States Patent
Lin

(10) Patent No.: US 10,813,964 B2
(45) Date of Patent: Oct. 27, 2020

(54) SHENLINGBAIZHU GRANULES AND PREPARATION METHOD THEREOF

(71) Applicant: BEIJING HANDIAN PHARMACEUTICAL CO., LTD., Beijing (CN)

(72) Inventor: Deliang Lin, Beijing (CN)

(73) Assignee: BEIJING HANDIAN PHARMACEUTICAL CO., LTD., Beijing (CN)

( * ) Notice: Subject to any disclaimer, the term of this patent is extended or adjusted under 35 U.S.C. 154(b) by 307 days.

(21) Appl. No.: 15/744,679

(22) PCT Filed: Aug. 22, 2016

(86) PCT No.: PCT/CN2016/096158
§ 371 (c)(1),
(2) Date: Jan. 12, 2018

(87) PCT Pub. No.: WO2017/032285
PCT Pub. Date: Mar. 2, 2017

(65) Prior Publication Data
US 2018/0207215 A1  Jul. 26, 2018

(30) Foreign Application Priority Data

Aug. 21, 2015 (CN) .......................... 2015 1 0520582

(51) Int. Cl.
| | |
|---|---|
| *A61K 36/258* | (2006.01) |
| *A61K 36/8945* | (2006.01) |
| *A61K 36/9064* | (2006.01) |
| *A61K 36/076* | (2006.01) |
| *A61K 36/284* | (2006.01) |
| *A61K 36/484* | (2006.01) |
| *A61K 36/62* | (2006.01) |
| *A61K 36/48* | (2006.01) |
| *A61P 1/00* | (2006.01) |
| *A61K 36/346* | (2006.01) |
| *A61K 36/8994* | (2006.01) |

(52) U.S. Cl.
CPC .......... *A61K 36/258* (2013.01); *A61K 36/076* (2013.01); *A61K 36/284* (2013.01); *A61K 36/346* (2013.01); *A61K 36/48* (2013.01); *A61K 36/484* (2013.01); *A61K 36/62* (2013.01); *A61K 36/8945* (2013.01); *A61K 36/8994* (2013.01); *A61K 36/9064* (2013.01); *A61P 1/00* (2018.01)

(58) Field of Classification Search
CPC .............. A61K 2300/00; A61K 36/076; A61K 36/258; A61K 36/284; A61K 36/346; A61K 36/48; A61K 36/484; A61K 36/62; A61K 36/8945; A61K 36/8994; A61K 36/9064; A61P 1/00
See application file for complete search history.

(56) References Cited

FOREIGN PATENT DOCUMENTS

| CN | 1788783 A | 6/2006 |
|---|---|---|
| CN | 101934045 A | 1/2011 |
| CN | 105056092 A | 11/2015 |
| CN | 110051791 A | * 7/2019 |

OTHER PUBLICATIONS

International Search Report dated Oct. 20, 2016 for corresponding PCT Application No. PCT/CN2016/096158, with English Translation (5 pages).

* cited by examiner

*Primary Examiner* — Aaron J Kosar
(74) *Attorney, Agent, or Firm* — Lewis Roca Rothgerber Christie LLP

(57) ABSTRACT

Disclosed are shenlingbaizhu granules and a preparation method thereof, wherein the shenlingbaizhu granules comprise an extract of raw material medicines and excipients, the raw material medicines being: 400 parts by weight of ginseng, 400 parts by weight of tuckahoe, 400 parts by weight of *Rhizoma atractylodis macrocephalae* stir-fried with bran, 400 parts by weight of yam, 300 parts by weight of fried white hyacinth bean, 200 parts by weight of lotus seed, 200 parts by weight of coix seed stir-fried with bran, 200 parts by weight of *Fructus amomi*, 200 parts by weight of *Platycodon grandiflorum*, and 400 parts by weight of licorice, wherein the excipients comprise citric acid, stevioside and lactose, and the granules are dispersed by adding an appropriate amount of water and then obtaining a clear solution.

14 Claims, No Drawings

SHENLINGBAIZHU GRANULES AND PREPARATION METHOD THEREOF

CROSS-REFERENCE TO RELATED APPLICATION(S)

This application is a National Phase Patent Application and claims priority to and the benefit of International Application Number PCT/CN2016/096158, filed on Aug. 22, 2016, which claims priority to Chinese Patent Application Number 201510520582.0, filed on Aug. 21, 2015, the entire contents of all of which are incorporated herein by reference.

TECHNICAL FIELD

The present invention belongs to the field of traditional Chinese medicine preparation, and in particular relates to new shenlingbaizhu granules which are used for invigorating spleen and stomach and benefiting lung qi and especially for treating weakness of spleen and stomach, anorexia and loose stools, short breath and cough and/or limb tiredness and hypodynamia in a child, and a preparation method thereof.

BACKGROUND OF THE INVENTION

Shenlingbaizhu granules, described in *Pharmacopoeia of The People's Republic of China*, have efficacy of invigorating spleen and stomach, and replenishing and restoring lung qi, and are used for treating weakness of the spleen and stomach, anorexia and loose stools, short breath and cough, and/or limb tiredness and hypodynamia. The prescription composition is as follows:

*Radix ginseng* 400 g, *Poria* 400 g, stir-baked *Rhizoma atractylodis macrocephalae* in bran 400 g, *Rhizoma dioscoreae* 400 g, fried *Semen dolichoris album* 300 g, *Semen nelumbinis* 200 g, stir-baked *Semen coicis* in bran 200 g, *Fructus amomi villosi* 200 g, *Radix platycodonis* 200 g, *Radix glycyrrhizae* 400 g.

The preparation method of shenlingbaizhu granules has been described in many prior arts. For example, the preparation process of shenlingbaizhu granules recorded in the ministry Traditional Chinese Medicine Prescription Preparation (Volume twenty) comprises following steps: extracting volatile oils from the *Fructus amomi villosi* and the *Rhizoma atractylodis macrocephalae*, and collecting aqueous solutions obtained upon distillation in another container, respectively; adding water to residues and other eight raw material medicines including the *Radix ginseng* and the like and decocting them in the water, filtering decoction obtained, and combining the filtrate with the aqueous solution as above and concentrating into a clear paste; then, combining 1 part of the clear paste, 2 parts of sucrose, 2.5 parts of dextrin and a proper amount of ethanol and granulating, drying, and adding therein the *Rhizoma atractylodis macrocephalae* volatile oil and the *Fructus amomi villosi* volatile oil as above, and uniformly mixing, thereby obtaining shenlingbaizhu granules. The process is not entirely reasonable, because saponin ingredients contained in the *Rhizoma dioscoreae*, the *Radix ginseng*, the *Radix platycodonis* and the like cannot be fully extracted with water.

As another example, Chinese patent application publication N. CN1788783A (publication date: Jun. 21, 2006) discloses a preparation method of shenlingbaizhu granules. The process in detail is as follows: preparing the ten raw material medicines as above and crushing the *Rhizoma dioscoreae* into fine powders for later use; extracting volatile oil from the *Fructus amomi villosi* and collecting aqueous solution obtained upon distillation in another container; adding 4 times amount of 95% ethanol into residues, the *Radix ginseng* and the stir-baked *Rhizoma atractyldis macrocephalae* in bran and soaking them in the ethanol for 24 hours, followed by heating under reflux for 3 hours, and filtering; after recovery of ethanol, concentrating the filtrate to obtain a clear paste with a relative density of 1.0 (65° C.); and further, adding 4 times amount of 50% ethanol into the filter residues and heating under reflux for 3 hours, filtering, and after recovery of ethanol, concentrating the filtrate to obtain a clear paste with a relative density of 1.12 to 1.13 (80° C.), and reserving the filter residues for later use; adding 8 times amount of water into the rest six raw material medicines including *Poria* and the like and decocting them in the ethanol for 2 hours and filtering, and adding 8 times amount of water into the filter residues and the filter residues as above and decocting them in water for 1.5 hours, and filtering; combining the filtrates and the aqueous solution as above, filtering, and concentrating the filtrate until its relative density is 1.2 (80° C.); adding therein the two clear pastes as above and further concentrating to obtain a thick paste with a relative density of 1.30 to 1.34 (80° C.); then adding the *Rhizoma dioscoreae* fine powder sieved through a 100-mesh sieve, uniformly mixing, drying the mixture at a low temperature of 60° C. and crushing; and mixing 1 part of the dry paste and 0.4 parts of lactose powders uniformly, granulating with 70% ethanol, spraying therein the *Fructus amomi villosi* volatile oil, and uniformly mixing, thereby obtaining 1000 g granules in total.

Those shenlingbaizhu granules prepared by the methods as above are subpackaged with 3 g per bag, and are taken three times a day with 2 to 3 g per time. In clinical practice, shenlingbaizhu granules have a good effect on children's weakness of spleen and stomach. However, turbid medicine liquor will be formed when adding water into the shenlingbaizhu granules of the prior arts as above, which has a poor sensory impression and a bad taste, making children reluctant to take and therefore resulting in a poor compliance.

In addition, those shenlingbaizhu granules of the prior arts as above have no unit dose packages for children, and as for adult preparations, usage and dosage for children are not provided either, resulting in non-standard applications and inaccurate dosages of those preparations for children. In case dosage is insufficient, corresponding curative effect would be compromised, and period of treatment and rehabilitation may be prolonged. Therefore, it is necessary to provide shenlingbaizhu granules which are specially suitable for children to take; and to improve the preparation method of shenlingbaizhu granules, which on one hand in order to improve curative effect, and on the other hand to improve the compliance of children, thereby meeting the requirements of clinical child medication.

SUMMARY OF THE INVENTION

For the problems existing in the prior art, the present invention provides a new kind of shenlingbaizhu granules and a preparation method thereof. A clear solution which has a good taste can be obtained after dispersion by adding a proper amount of water into the new shenlingbaizhu granules; thereby the medication compliance for children can be improved. In addition, the new shenlingbaizhu granules of the present invention have an overall clinical efficacy comparable to the prior art granules, but have a significantly stronger effect on the improvement in children's weakness of spleen and stomach than the prior art granules; and also, specific usage and dosage are established for children in the present invention.

In order to achieve the above objects, following technical solutions are provided in the present invention:

Shenlingbaizhu granules comprising an extract of raw material medicines and excipients; wherein the raw material medicines include 400 parts by weight of *Radix ginseng*, 400 parts by weight of *Poria*, 400 parts by weight of stir-baked *Rhizoma atractyldis macrocephalae* in bran, 400 parts by weight of *Rhizoma dioscoreae*, 300 parts by weight of stir-fried *Semen dolichoris album*, 200 parts by weight of *Semen nelumbinis*, 200 parts by weight of stir-baked *Semen coicis* in bran, 200 parts by weight of *Fructus amomi villosi*, 200 parts by weight of *Radix platycodonis* and 400 parts by weight of *Radix glycyrrhizae*, and the excipients include citric acid, stevioside and lactose; and wherein a clear solution can be obtained after dispersion by adding a proper amount of water into the shenlingbaizhu granules.

Preferably, the shenlingbaizhu granules are administered to a 3-5 years old child in need 3 times a day with 1 g per time; and are administered to a 5-14 years old child in need 3 times a day with 2 g per time.

Another object of the present invention is to provide a preparation method of the shenlingbaizhu granules as above, which raw material medicines include:

400 parts by weight of *Radix ginseng*, 400 parts by weight of *Poria*, 400 parts by weight of stir-baked *Rhizoma atractyldis macrocephalae* in bran, 400 parts by weight of *Rhizoma dioscoreae*, 300 parts by weight of stir-fried *Semen dolichoris album*, 200 parts by weight of *Semen nelumbinis*, 200 parts by weight of stir-baked *Semen coicis* in bran, 200 parts by weight of *Fructus amomi villosi*, 200 parts by weight of *Radix platycodonis* and 400 parts by weight of *Radix glycyrrhizae*;

wherein the preparation method includes following steps:

(1) preparing the raw material medicines as above;

(2) extracting the *Fructus amomi villosi* using steam distillation method to obtain *Fructus amomi villosi* volatile oil, collecting aqueous solution obtained upon distillation in another container, and reserving residues for later use;

(3) adding 80-95% ethanol into the residues obtained from step (2) with the *Radix ginseng*, the *Rhizoma atractyldis macrocephalae*, and the *Radix platycodonis* and soaking them in the ethanol for 24 hours, the volume of the ethanol being 8-12 times the weight of the materials to be soaked, heating under refluxing for 2-3 hours, filtering, and after recovery of ethanol, concentrating the filtrate to obtain a clear paste with a relative density of 1.10-1.20 at 65° C.; and further, adding 30-60% ethanol into the filter residues and refluxing the filter residues in the ethanol for 2-3 hours, the volume of ethanol being 8-10 times the weight of the filter residues to be refluxed, filtering, and after recovery of ethanol, concentrating the filtrate to obtain a clear paste with a relative density of 1.10-1.20 at 80° C., and reserving the filter residues for later use;

(4) adding water into the filter residues obtained from step (3) with the *Poria*, the *Rhizoma dioscoreae*, the stir-fried *Semen dolichoris album*, the *Semen nelumbinis*, the stir-baked *Semen coicis* in bran and the *Radix glycyrrhizae* and decocting them in the water for two times with 1-3 hours for the first time, and 1-2 hours for the second time, the volume of water added per time being 8-12 times the weight of the materials to be decocted, combining the decoctions, filtering, and combining the filtrate with the aqueous solution obtained from step (2), allowing to stand, filtering, and concentrating the filtrate until its relative density is 1.15-1.30 at 80° C., and then adding therein the two clear pastes obtained from step (3), followed by further concentrating to obtain a clear paste with a relative density of 1.10-1.25 at 80° C., and spray-drying the clear paste to obtain spray-dried powders;

(5) adding into the spray-dried powders obtained from step (4) 0.5-1% of citric acid and 0.01-0.05% of stevioside for the weight of the spray-dried powders, as well as a proper amount of lactose, uniformly mixing, and granulating the mixture by dry granulation method, spraying therein the *Fructus amomi villosi* volatile oil obtained from step (2), uniformly mixing, and preparing the mixture into 1000 parts by weight of granules;

(6) subpackaging the granules obtained from step (5) with 1 g per bag.

Preferably, step (2) further comprises, before extracting the *Fructus amomi villosi* to obtain the *Fructus amomi villosi* volatile oil, adding water into the *Fructus amomi villosi* and soaking it in the water for 1 hour, the water added being 8-12 times the weight of the *Fructus amomi villosi*.

More preferably, step (2) further comprises, before extracting the *Fructus amomi villosi* to obtain the *Fructus amomi villosi* volatile oil, adding water into the *Fructus amomi villosi* and soaking it in the water for 1 hour, the water added being 10 times the weight of the *Fructus amomi villosi*.

Preferably, the *Fructus amomi villosi* is extracted using steam distillation method for 4-8 hours, preferably 6 hours, thereby obtaining the *Fructus amomi villosi* volatile oil.

Preferably, in step (3), the residues obtained from step (2) with the *Radix ginseng*, the *Rhizoma atractyldis macrocephalae* and the *Radix platycodonis* are extracted in 95% ethanol, and further, the filter residues are extracted in 50% ethanol.

Further preferably, in step (3), the volume of 95% ethanol is 8-10 times the weight of the materials, and the volume of the 50% ethanol is 8 times the weight of the filter residues.

As a preferred embodiment, the present invention provides a preparation method of shenlingbaizhu granules which raw material medicines include: 400 parts by weight of *Radix ginseng*, 400 parts by weight of *Poria*, 400 parts by weight of stir-baked *Rhizoma atractyldis macrocephalae* in bran, 400 parts by weight of *Rhizoma dioscoreae*, 300 parts by weight of stir-fried *Semen dolichoris album*, 200 parts by weight of *Semen nelumbinis*, 200 parts by weight of stir-baked *Semen coicis* in bran, 200 parts by weight of *Fructus amomi villosi*, 200 parts by weight of *Radix platycodonis* and 400 parts by weight of *Radix glycyrrhizae*;

wherein the preparation method includes following steps:

(1) preparing the raw material medicines as above;

(2) adding water into the *Fructus amomi villosi* and soaking it in the water for 1 hour, the water added being 10 times the weight of the *Fructus amomi villosi*, extracting the *Fructus amomi villosi* using steam distillation method for 6 hours, and collecting *Fructus amomi villosi* volatile oil for later use; collecting aqueous solution obtained upon distillation in another container for later use; and reserving residues for later use;

(3) adding 95% ethanol into the residues obtained in step (2) with the *Radix ginseng*, the *Rhizoma atractyldis macrocephalae*, and the *Radix platycodonis* and soaking them in the ethanol for 24 hours, the volume of the 95% ethanol being 8-10 times the weight of the materials to be soaked, heating under reflux for 3 hours, filtering, and after recovery of ethanol, concentrating the filtrate to obtain a clear paste with a relative density of 1.10-1.20 at 65° C.; and further, adding 50% ethanol into the filter residues and refluxing the filter residues in the ethanol for 3 hours, the volume of the 50% ethanol being 8 times the weight of the filter residues to be refluxed, filtering, and after recovery of ethanol, concentrating the filtrate to obtain a clear paste with a relative density of 1.10-1.20 at 80° C., and reserving the filter residues for later use;

(4) adding water into the filter residues obtained from step (3) with the *Poria*, the *Rhizoma dioscoreae*, the stir-fried *Semen dolichoris album*, the *Semen nelumbinis*, the stir-baked *Semen coicis* in bran and the *Radix glycyrrhizae* and decocting them in the water for two times with 2 hours for the first time and 1.5 hours for the second time, the volume of water added per time being 10 times the weight of the materials to be decocted, combining the decoctions, filtering, and combining the filtrate with the aqueous solution obtained from step (2), allowing to stand, filtering, and concentrating the filtrate until its relative density is 1.15-1.30 at 80° C., and then adding therein the two clear pastes obtained from step (3), followed by further concentrating to obtain a clear paste with a relative density of 1.15-1.20 at 80° C., and spray-drying the clear paste to obtain spray-dried powders;

(5) adding into the spray-dried powders obtained from step (4) 1% of citric acid and 0.01-0.05% of stevioside for the weight of the spray-dried powders, as well as a proper amount of lactose, uniformly mixing, and granulating the mixture by dry granulation method, spraying therein the *Fructus amomi villosi* volatile oil obtained from step (2), uniformly mixing, and preparing the mixture into 1000 parts by weight of granules;

(6) subpackaging the granules obtained from step (5) with 1 g per bag.

Another object of the present invention is to provide shenlingbaizhu granules prepared by the preparation method as above, wherein a clear solution can be obtained after dispersion by adding a proper amount of water into the shenlingbaizhu granules.

Obviously, the 1000 parts by weight of shenlingbaizhu granules obtained by using the preparation method according to the present invention comprise:

the spray-dried powders, the *Fructus amomi villosi* volatile oil, the 0.5-1% of citric acid (by weight for the spray-dried powders), and 0.01-0.05% of stevioside (by weight for the spray-dried powders), with the balance being lactose.

Due to the inevitable differences between different batches of raw material medicines, the amounts of the spray-dried powders and the *Fructus amomi villosi* volatile oil prepared by the preparation method of the present invention may vary, so the amount of lactose used for each batch may be adjusted accordingly depending on actual situations, so as to make the total amount of the granules be 1000 parts by weight.

Yet another object of the present invention is to provide an administration method of shenlingbaizhu granules as above. Preferably, the shenlingbaizhu granules are prepared by the preparation method as above, and the administration method includes administering the shenlingbaizhu granules to a child suffering from weakness of spleen and stomach, anorexia and loose stools, short breath and cough, and/or limb tiredness and hypodynamia, wherein a 3-5 years old child is administered 3 times a day with 1 g per time, and a 5-14 years old child is administered 3 times a day with 2 g per time.

In addition, still another object of the present invention is to provide use of the shenlingbaizhu granules as above or the shenlingbaizhu granules prepared by the preparation method as above in the manufacture of a medicament for treatment of a child suffering from weakness of spleen and stomach, anorexia and loose stools, short breath and cough, and/or limb tiredness and hypodynamia.

Of course, the shenlingbaizhu granules provided by the present invention not only can be used in a child suffering from weakness of spleen and stomach, anorexia and loose stools, short breath and cough, and/or limb tiredness and hypodynamia, but also can be used in an adult suffering from or having those conditions and symptoms. When the granules are used by an adult, only the dosage has to be increased accordingly. Generally, the dosage for an adult is three times a day with a dosage of 3 g per time.

The "parts by weight" used in the present invention refers to the proportional relationship by weight among those raw material medicines and the proportional relationship by weight of the finally prepared shenlingbaizhu granules. According to actual situations, 1 part by weight can be 1 g, 1 kg, 100 g, or any other mass (such as 20 g, 50 g and the like). When 1 part by weight is 1 g, 1000 g shenlingbaizhu granules may be prepared according to the preparation method as above, and can be subpackaged into 1000 bags with 1 g per bag.

The concentration of ethanol mentioned in the specification of the present invention, such as 80-95% ethanol, 30-60% ethanol, 95% ethanol, 50% ethanol, etc., refers to the volume percentage concentration.

Beneficial technical effects of the present invention are as follows:

1. Medication compliance of children is higher than that of the prior art preparations. Determination results from Effect Example 1 showed that the granules of the present invention had better dissolubility and mouth feel than each Comparative Example, and children acceptance was also significantly higher than that of each Comparative Example.

2. The granules prepared by the present invention have high contents of active ingredients, indicating that the extraction efficiency is high and the medicine efficacy can be better guaranteed. The content of polysaccharide determined in Effect Example 2 and the content of ginsenoside Rg1 determined in Effect Example 3 showed that, both the granules prepared in the present invention and Comparative Example 3 (shulingbaizhu granules disclosed in Patent Publication No. CN1788783A) had higher contents than those prepared in Comparative Examples 1 and 2, and Example 1 achieved the highest content and therefore was a preferred embodiment.

3. Results of clinical application showed that, the shenlingbaizhu granules of the present invention achieved higher overall effective rate and cure rate for children suffering from weakness of spleen and stomach than those prepared in Comparative Example 3, and had a better efficacy than those prepared in Comparative Example 3 in improving the stool frequency of the children, and the symptoms such as lassitude and short breath of the children were significantly improved with the granules of the present invention. It is indicated that the shenlingbaizhu granules prepared by the present invention have a better efficacy.

4. Currently, commercially available shenlingbaizhu granules are only provided for adult use with usage, dosage and packaging specifications intended for adults. The present invention establishes usage, dosage levels and specific packaging specifications for children of different ages, and therefore children will be provided with a more convenient and accurate administration of shenlingbaizhu granules.

THE PREFERRED EMBODIMENTS OF THE PRESENT INVENTION

The present invention will be described by reference to specific embodiments. A person skilled in the art can under-stand that these embodiments are used only to illustrate the present invention and do not limit the scope of the present invention in any way.

Raw materials, reagents, including raw material medicines and the like in the following examples are purchased from public commercial channels, unless otherwise specified. Experimental methods used in the following examples and experimental examples are all conventionally used techniques in the art, unless otherwise specified.

Shenlingbaizhu granules in the following Examples and Comparative Examples are prepared from the same raw material medicines which are as follows:

Radix ginseng 400 g, Poria 400 g, Rhizoma atractylodis macrocephalae (stir-baked in bran) 400 g, Rhizoma dioscoreae 400 g, Semen dolichoris album (stir-baked) 300 g, Radix platycodonis 200 g, Semen nelumbinis 200 g, Semen coicis (stir-baked) 200 g, Fructus amomi villosi 200 g, Radix glycyrrhizae 400 g.

The place of origin and supplier of each of the raw material medicines are shown in the following Table:

| Raw material medicine | Place of origin (China) | Supplier |
| --- | --- | --- |
| Radix Ginseng | Jilin | Beijing Huamiao Chinese Medicine Engineering Technology Development Center |
| Fructus Amomi Villosi | Hainan | Haozhou Holyou Chinese Herbal Pieces Co., Ltd. |
| Radix Platycodonis | Neimeng | Haozhou Holyou Chinese Herbal Pieces Co., Ltd. |
| Poria | Anhui | Haozhou Holyou Chinese Herbal Pieces Co., Ltd. |
| Rhizoma Atractylodis Macrocephalae (stir-baked) | Zhejiang | Haozhou Holyou Chinese Herbal Pieces Co., Ltd. |
| Rhizoma Dioscoreae | Hebei | Haozhou Holyou Chinese Herbal Pieces Co., Ltd. |
| Semen Dolichoris Album (stir-baked) | Guangxi | Haozhou Holyou Chinese Herbal Pieces Co., Ltd. |
| Semen Nelumbinis | Hunan | Haozhou Holyou Chinese Herbal Pieces Co., Ltd. |
| Stir-baked Semen Coicis in bran | Guizhou | Haozhou Holyou Chinese Herbal Pieces Co., Ltd. |
| Radix Glycyrrhizae | Gansu | Haozhou Holyou Chinese Herbal Pieces Co., Ltd. |

Example 1 Preparation Method of Shenlingbaizhu Granules and the Shenlingbaizhu Granules Prepared by the Same The preparation method included following steps:

(1) The raw material medicines were prepared as above.

(2) 10 times amount of water was added into the Fructus amomi villosi to soak it for 1 hour. Then the Fructus amomi villosi was extracted using steam distillation method for 6 hours, and Fructus amomi villosi volatile oil obtained was collected for later use. Also, the aqueous solution obtained upon distillation was collected in another container for later use, and the residues were reserved for later use too.

(3) 10 times amount of 95% ethanol (a ratio of volume to weight) was added into the residues obtained from step (2) with the Radix ginseng, the Rhizoma atractyldis macrocephalae and the Radix platycodonis to soak them for 24 hours. Then the materials were heated under reflux for 3 hours, filtered, and after recovery of ethanol, the filtrate was concentrated to obtain a clear paste with a relative density of 1.15-1.20 (65° C.). Further, 8 times amount of 50% ethanol (a ratio of volume to weight) was added into the filter residues and the filter residues was refluxed in the ethanol for 3 hours, filtered, and after recovery of ethanol, the filtrate was concentrated to obtain a clear paste with a relative density of 1.12-1.13 (80° C.). Also, the filter residues were reserved for later use.

(4) Water was added into the filter residues obtained from step (3) with the rest six raw material medicines including Poria and the like to decoct them for two times with 2 hours for the first time and 1.5 hours for the second time, the volume of water added per time being 10 times the weight of the materials to be decocted (a ratio of volume to weight). Decoctions were combined, filtered, and the filtrate was combined with the aqueous solution obtained from step (2). The combined mixture was allowed to stand, filtered, and the filtrate was concentrated until its relative density was 1.20-1.25 (80° C.). Then the two clear pastes obtained from step (3) were added therein, and the obtained mixture was further concentrated to obtain a clear paste with a relative density of 1.15-1.20 (80° C.). The clear paste was spray-dried and 850 g spray-dried powders were obtained.

(5) 8.5 g citric acid, 0.09 g stevioside and 114.43 g lactose were added into the spray-dried powders obtained from step (4), and they were uniformly mixed, and granulated by dry granulation method. Then the Fructus amomi villosi volatile oil obtained from step (2) was sprayed therein, uniformly mixed and the mixture was prepared into 1000 g granules.

(6) The granules obtained from step (5) were subpackaged with 1 g per bag.

The shenlingbaizhu granules prepared by the preparation method as above have following functions and indications: the granules invigorate spleen and stomach, and replenish and restore lung qi; and are used to treat children's weakness of spleen and stomach, anorexia and loose stools, short breath and cough, and/or limb tiredness and hypodynamia. The granules can be used as follows: a 3-5 years old child is administered 3 times a day with 1 g per time, and a 5-14 years old child is administered 3 times a day with 2 g per time.

Example 2 Preparation Method of Shenlingbaizhu Granules and the Shenlingbaizhu Granules Prepared by the Same The preparation method included following steps:

(1) The raw material medicines were prepared as above.

(2) 8 times amount of water was added into the Fructus amomi villosi to soak it for 1 hour. Then the Fructus amomi villosi was extracted using steam distillation method for 8 hours, and Fructus amomi villosi volatile oil obtained was collected for later use. Also, the aqueous solution obtained upon distillation was collected in another container for later use, and the residues were reserved for later use too.

(3) 12 times amount of 95% ethanol (a ratio of volume to weight) was added into the residues obtained from step (2) with the Radix ginseng, the Rhizoma atractyldis macrocephalae and the Radix platycodonis to soak them for 24 hours. Then the materials were heated under reflux for 3 hours, filtered, and after recovery of ethanol, the filtrate was concentrated to obtain a clear paste with a relative density of 1.10-1.15 (65° C.). Further, 10 times amount of 30% ethanol (a ratio of volume to weight) was added into the filter residues and the filter residues was refluxed in the ethanol for 2 hours, filtered, and after recovery of ethanol, the filtrate was concentrated to obtain a clear paste with a relative density of 1.12-1.13 (80° C.). Also, the filter residues were reserved for later use.

(4) Water was added into the filter residues obtained from step (3) with the rest six raw material medicines including *Poria* and the like to decocte them for two times with 3 hours for the first time and 2 hours for the second time, the volume of water added per time being 12 times the weight of the materials to be decocted (a ratio of volume to weight). Decoctions were combined, filtered, and the filtrate was combined with the aqueous solution obtained from step (2). The combined mixture was allowed to stand, filtered, and the filtrate was concentrated until its relative density was 1.15-1.20 (80° C.). Then the two clear pastes obtained from step (3) were added therein, and the obtained mixture was further concentrated to obtain a clear paste with a relative density of 1.15-1.20 (80° C.). The clear paste was spray-dried and 870 g spray-dried powders were obtained.

(5) 8.7 g citric acid, 0.09 g stevioside and 120.4 g lactose were added into the spray-dried powders obtained from step (4), and they were uniformly mixed, and granulated by dry granulation method. Then the *Fructus amomi villosi* volatile oil obtained from step (2) was sprayed therein, uniformly mixed and the mixture was prepared into 1000 g granules.

(6) The granules obtained from step (5) were subpackaged with 1 g per bag.

The shenlingbaizhu granules prepared by the preparation method as above have following functions and indications: the granules invigorate spleen and stomach, and replenish and restore lung qi; and are used to treat children's weakness of spleen and stomach, anorexia and loose stools, short breath and cough, and/or limb tiredness and hypodynamia. The granules can be used as follows: a 3-5 years old child is administered 3 times a day with 1 g per time, and a 5-14 years old child is administered 3 times a day with 2 g per time.

Example 3 Preparation Method of Shenlingbaizhu Granules and the Shenlingbaizhu Granules Prepared by the Same The preparation method included following steps:

(1) The raw material medicines were prepared as above.

(2) 12 times amount of water was added into the *Fructus amomi villosi* to soak it for 1 hour. Then the *Fructus amomi villosi* was extracted using steam distillation method for 4 hours, and *Fructus amomi villosi* volatile oil obtained was collected for later use. Also, the aqueous solution obtained upon distillation was collected in another container for later use, and the residues were reserved for later use too.

(3) 8 times amount of 85% ethanol (a ratio of volume to weight) was added into the residues obtained from step (2) with the *Radix ginseng*, the *Rhizoma atractyldis macrocephalae* and the *Radix platycodonis* to soak them for 24 hours. Then the materials are heated under reflux for 2.5 hours, filtered, and after recovery of ethanol, the filtrate was concentrated to obtain a clear paste with a relative density of 1.10-1.15 (65° C.). Further, 60% ethanol was added into the filter residues and the filter residues was refluxed in the ethanol for 3 hours, filtered, and after recovery of ethanol, the filtrate was concentrated to obtain a clear paste with a relative density of 1.12-1.13 (80° C.). Also, the filter residues were reserved for later use.

(4) Water was added into the filter residues obtained from step (3) with the rest six raw material medicines including *Poria* and the like to decocte them for two times with 1 hour for the first time and 1 hour for the second time, the volume of water added per time being 8 times the weight of the materials to be decocted (a ratio of volume to weight). Decoctions were combined, filtered, and the filtrate was combined with the aqueous solution obtained from step (2). The combined mixture was allowed to stand, filtered, and the filtrate was concentrated until its relative density was 1.25-1.30 (80° C.). Then the two clear pastes obtained from step (3) were added therein, and the obtained mixture was further concentrated to obtain a clear paste with a relative density of 1.15-1.20 (80° C.). The clear paste was spray-dried and 840 g spray-dried powders were obtained.

(5) 8.4 g citric acid, 0.08 g stevioside and 151.52 g lactose were added into the spray-dried powders obtained from step (4), and they were uniformly mixed, and granulated by dry granulation method. Then the *Fructus amomi villosi* volatile oil obtained from step (2) was sprayed therein, uniformly mixed and the mixture was prepared into 1000 g granules.

(6) The granules obtained from step (5) were subpackaged with 1 g per bag.

The shenlingbaizhu granules prepared by the preparation method as above have following functions and indications: the granules invigorate spleen and stomach, and replenish and restore lung qi; and are used to treat children's weakness of spleen and stomach, anorexia and loose stools, short breath and cough, and/or limb tiredness and hypodynamia. The granules are used as follows: a 3-5 years old child is administered 3 times a day with 1 g per time, and a 5-14 years old child is administered 3 times a day with 2 g per time.

Comparative Example 1 Shenlingbaizhu Oral Solution

Shenlingbaizhu oral solution was prepared by the method as follows:

(1) The *Radix ginseng* was crushed into fine powders, and 1400 ml and 1000 ml 50% ethanol were added therein respectively and heated under reflux for extraction twice (reflux temperature and reflux rate were adjusted as appropriate), with the first refluxing time being 1.5 hours and the second refluxing time being 1 hour. The reflux extracts were filtered using a filter, and filtrates were combined. Ethanol was recovered under reduced pressure from the combined filtrate until it became syrupy and a concentrate solution was obtained and refrigerated for later use.

(2) The *Rhizoma atractylodis macrocephalae* and the *Fructus amomi villosi* were placed in water vapor for distillation, and then volatile oil and distillate were collected.

(3) Residues obtained from reflux extraction of the *Radix ginseng*, residues obtained from distillation of the *Rhizoma atractylodis macrocephalae* and the *Fructus amomi villosi* were placed together with other seven raw material medicines in a decoction pot and decoction was performed twice, with 1800 ml water added for each time and 1.5 hours and 1 hour respectively. Decoctions were collected, filtered, and the filtrate was concentrated into syrupy, and then a proper amount of ethanol was added to obtain a mixture having an ethanol content of 65%. The mixture was refrigerated and allowed to stand. Then, the supernatant obtained was filtered, and a concentrated solution was obtained after recovering ethanol under reduced pressure from the filtrate until it became syrupy.

(4) The concentrated solutions obtained from step (1) and step (3) were uniformly mixed and a proper amount of water was added therein. The obtained mixture was stirred, allowed to stand and filtered. The volatile oil and the distillate obtained from step (2) were added into the filtrate, before proper amounts of tween-80 and sorbitol were added. Then additional water was added, reaching a total volume of 3300 ml, and a solution was formed. Afterwards, the solution was filtered, and the filtrate was put into vials which subsequently were subjected to hot-pressure sterilization and packaging to obtain the shenlingaizhu oral solution.

Comparative Example 2 Shenlingbaizhu Granules

Shenlingbaizhu granules were prepared by the method as follows:

(1) Raw material medicines were prepared as above.

(2) 10 times amount of water was added into the *Fructus amomi villosi* and the *Rhizoma atractylodis macrocephalae* to extract volatile oils respectively by distillation for 6 hours. Aqueous solution obtained upon distillation was collected in another container.

(3) Water was added into residues obtained from step (2) with the eight raw material medicines including *Radix ginseng* and the like to decoct them for three times, with 1.5 hours for the first time and 1 hour for the second or the third time, the volume of water added for each time being 10 times the weight of the materials to be decocted. Decoctions were combined, filtered, and the filtrate was combined with the aqueous solution as above to obtain a mixture. The mixture was concentrated to obtain a clear paste with a relative density of 1.20-1.25 at 55° C.

(4) 1 part of the clear paste, 2 parts of sucrose, 2.5 parts of dextrin and a proper amount of ethanol were mixed, granulated, and dried. Then the *Rhizoma atractylodis macrocephalae* volatile oil and the *Fructus amomi villosi* volatile oil were added therein, uniformly mixed, and the mixture was subpackaged with 6 g per bag.

Functions and indications: the granules invigorate spleen and stomach, and replenish and restore lung qi; and are used to treat children's weakness of spleen and stomach, anorexia and loose stools, short breath and cough, and/or limb tiredness and hypodynamia.

Usage and dosage: the granules are taken along with boiled water, three times a day with 6 g per time.

Comparative Example 3 Shenlingbaizhu Granules (1) Raw material medicines were prepared as above;

(2) The *Rhizoma dioscoreae* was crushed into fine powders for later use;

(3) 10 times amount of water was added into the *Fructus amomi villosi* to extract volatile oil by distillation. Aqueous solution obtained upon distillation was collected in another container.

(4) 4 times amount of 95% ethanol was added into residues obtained from step (2) with *Radix ginseng* and *Rhizoma atractyldis macrocephalae* to soak them for 24 hours. Then the materials were heated under reflux for 3 hours, filtered, and after recovery of ethanol, the filtrate was concentrated to obtain a clear paste with a relative density of 1.0 (65° C.). Further, 4 times amount of 50% ethanol was added into the filter residues and the filter residues were refluxed for 3 hours, filtered, and after recovery of ethanol, the filtrate was concentrated to obtain a clear paste with a relative density of 1.12-1.13 (80° C.). Also, the filter residues were reserved for later use.

(5) 8 times amount of water was added into the rest six raw material medicines including *Poria* and the like to decoct them for 2 hours. Decoction was filtered, and the filter residues were combined with the filter residues obtained from step (4). Then 8 times amount of water was added into the combined residues to decoct them for 1.5 hours, and decoction obtained was filtered. Two filtrates obtained were combined with the aqueous solution as above, filtered, and the filtrate was concentrated until its relative density is 1.2 (80° C.). The two clear pastes obtained from step (4) were added therein, and the obtained mixture was further concentrated to obtain a thick paste with a relative density of 1.30-1.34 (80° C.).

(6) The *Rhizoma dioscoreae* fine powders were sieved through a 100-mesh sieve and added into the thick paste obtained from step (5). They were uniformly mixed, dried at a low temperature of 60° C., and crushed. 1 part of the dry paste and 0.4 parts of lactose powders were uniformly mixed and granulated with 70% ethanol. The *Fructus amomi villosi* volatile oil was sprayed therein, and uniformly mixed. 1000 g granules in total were obtained, and subpackaged with 3 g per bag, thereby obtaining the shenlingbaizhu granules.

Functions and indications: the granules invigorate spleen and stomach, and replenish and restore lung qi; and are used to treat children's weakness of spleen and stomach, anorexia and loose stools, short breath and cough, and/or limb tiredness and hypodynamia.

Usage and dosage: the granules are taken along with boiled water, three times a day with 2-3 g per time.

Effect Example 1 Determinations of the Dissolubility and Taste of the Shenlingbaizhu Granules Prepared in Examples 1-3 and Comparative Examples 1-3

Dissolubility of the samples of shenlingbaizhu granules prepared in Examples 1-3 and Comparative Examples 2-3 were determined according to the determination method under "Granules" in General provision 0104, *Pharmacopoeia of The People's Republic of China*, 2015 Edition (200 ml water was added to each bag of granules).

In addition, five children were selected for taste determination of the samples prepared in Examples 1-3 and Comparative Examples 1-3. Each sample was scored for acceptance: 5 represents fully acceptable, the acceptance represented by 4, 3 and 2 decreases gradually, and 1 represents not acceptable; and mean value of the scores was taken as the acceptance score of each group of samples.

The results were shown in Table 1.

TABLE 1

Determination results of dissolubility and taste

| Sample | Dissolubility | Taste | Acceptance |
|---|---|---|---|
| Example 1 | all dissolved, solution clear, and storage without precipitation | sour-sweet | 5.0 |
| Example 2 |  |  | 5.0 |
| Example 3 |  |  | 5.0 |
| Comparative Example 1 | — | slightly bitter | 2.5 |
| Comparative Example 2 | clear, and storage without precipitation | slightly bitter | 2.5 |
| Comparative Example 3 | turbid, and storage with a large amount of precipitations | slightly bitter | 1.0 |

Conclusion: the shenlingbaizhu granules prepared in Examples 1-3 of the present invention had a significantly better dissolubility than those prepared in Comparative Example 3; had a sour-sweet taste, and were significantly more acceptable to children than those prepared in Comparative Examples 1-3. As for the granules prepared in Comparative Example 3, when water added, a large amount of precipitations appeared in the solution which had a poor taste to children, and was difficult to be swallowed, and so the acceptance is the lowest.

Therefore, the experimental results as above show that the shenlingbaizhu granules of the present invention are more suitable for children.

Effect Example 2 Determination of the Content of Polysaccharide in Preparations of Examples 1-3 and Comparative Examples 1-3

Raw material medicines such as *Poria, Radix ginseng* and the like in the prescription of shenlingbaizhu granules contain polysaccharide which can improve body's immunity, and polysaccharide levels can be used as one of the indicators of drug efficacy. Therefore, the content of polysaccharide in the preparations prepared in Examples and Comparative Examples was determined by following method.

Experiment Method:

Preparation of Reference Solution 50 mg anhydrous glucose reference sample was precisely weighed and dried at 105° C. to achieve a constant weight. Then the sample was dissolved in added ultrapure water and was made into a 50 ml solution in a 50 ml volumetric flask. The flask was uniformly shaken and 5 ml of the solution was precisely pipetted into another 50 ml volumetric flask, diluted with ultrapure water to obtain a glucose reference solution of 0.1 mg/ml.

Drawing of Standard Curve

Each of 0, 0.1, 0.2, 0.4, 0.6, 0.8 and 1.0 mL of the glucose reference solution as above was precisely pipetted into a 50 ml volumetric flask respectively, into which water was added to reach the scale line. The volumetric flasks were shaken evenly, and then 2 ml of the solution was precisely pipetted from each flask into a test tube with a stopper respectively. 1 ml of 4% phenol solution was added into each test tube, uniformly mixed, and then 7.0 ml sulfuric acid was added quickly into each test tube. The test tubes were shaken evenly, and then placed in a water bath at 40° C. for 30 minutes before taken out and placed in an ice water bath for 5 minutes. Afterwards, all the test tubes were taken out, and setting the solution in the first test tube containing 0 mL of the glucose reference solution as the blank, the absorbance at the wavelength of 490 nm of each solution was determined spectrophotometrically according to General provision 0401, *Pharmacopoeia of The People's Republic of China*, 2015 Edition. A standard curve was drawn by using the absorbance as the vertical coordinate and the concentration as the horizontal coordinate.

Determination Method 1 g (or 1 ml) of the sample from each of Examples 1-3 and Comparative Examples 2-3 (moisture in each additional sample powders was also determined according to General provision 0832, *Pharmacopoeia of The People's Republic of China*, 2015 Edition) was precisely weighed and placed into a 100 ml volumetric flask. Then each sample was dissolved in added water and was made into a solution reaching the scale line and shaken evenly. 2 ml of each of the solutions was precisely weighed from the flasks, into which 10 mL ethanol was added and stirred. Afterwards, each of the solutions was centrifuged, and the pellets obtained were dissolved in added water, and then placed in a 50 mL volumetric flask and diluted with water to reach the scale line. 2 mL of each of the solutions was precisely pipetted from each flask, and following the procedure described under "Drawing of standard curve" which read from "1 ml of 4% phenol solution was added", the absorbance was determined, and the content of polysaccharide in each sample solution was obtained by reference to the standard curve.

Results: shown in Table 2.

TABLE 2

Determination results of the content of polysaccharide

| Group | Content of polysaccharide (mg/g or mg/ml) |
|---|---|
| Example 1 | 768.39 |
| Example 2 | 742.05 |
| Example 3 | 747.63 |
| Comparative Example 1 | 56.8 |
| Comparative Example 2 | 371.76 |
| Comparative Example 3 | 743.18 |

Conclusions: the contents of polysaccharide in the oral solution prepared in Comparative Example 1 and in the granules prepared in Comparative Example 2 were significantly lower than those in other samples, indicating that the polysaccharide cannot be extracted sufficiently using the preparation methods of Comparative Example 1 and Comparative Example 2, which is unfavorable to the full play of medicinal efficacy. The polysaccharide content per grain of granules of Examples 1 to 3 and that of Comparative Example 3 were substantially the same, among which the content of Example 1 was the highest, indicating that the preparation method of Example 1 is a more preferable technical solution for extraction of polysaccharide.

Effect Example 3 Determination of the Content of Ginsenoside Rg1 in Preparations of Examples and Comparative Examples The content of ginsenoside Rg1 was determined according to high performance liquid chromatography method (General provision 0512, *Pharmacopoeia of The People's Republic of China*, 2015 Edition).

Chromatographic Conditions and System Suitability Test

Octadecylsilane chemically bonded silica (ODS) was used as the filler, acetonitrile-0.1% phosphoric acid (18: 82) was used as the mobile phase, the detection wavelength was 203 nm, and the theoretical plate number calculated by the ginsenoside Rg1 peak should not be less than 2500.

Preparation of Reference Solution

A proper amount of ginsenoside Rg1 reference sample was precisely weighed and dissolved in added methanol to prepare a solution containing 0.3 mg ginsenoside Rg1 per 1 mL.

Preparation of Test Solution

Granules were taken and finely ground. 10.0 g the ground granules were precisely weighed, into which 100 mL methanol was added, and then weighed together before heating under reflux for 1 hour. When cooled, weight was measured again, and methanol was added to supplement weight loss, before being shaken evenly and filtered. 50 ml of subsequent filtrate obtained was precisely weighed and evaporated to dryness in an evaporating dish, and 50 ml water was added into the residue to get a solution. Then the solution was extracted twice with petroleum ether (60-90° C.), 30 mL each time. The ether solution was discarded, and the aqueous solution was extracted under shaking with water saturated n-butyl alcohol for 5 times (30 ml, 25 ml, 25 ml, 20 ml, 20 ml, respectively). The n-butyl alcohol extraction solutions were combined, and then extracted twice with 1% NaOH solution, 20 mL each time. The alkali liquor was discarded, and the remainder was washed twice with water saturated with n-butyl alcohol, 20 mL each time. Then the n-butyl alcohol solution obtained was evaporated to dryness, and the residue was dissolved in added methanol and transferred to a 5 mL volumetric flask. Methanol was added into the flask to reach the scale line, and shaken evenly. The solution obtained was filtered through a microporous membrane (0.45 μm), thereby obtaining the test solution.

10 ml of oral solution was taken into which water was added to 50 ml. Following the procedure described above which read from "extracting twice by adding petroleum ether (60-90° C.) . . . ", the sample was prepared by the same method as the preparation of test solution of granules.

Determination

10 μl of the reference solution and 10 μl of each of test solutions were precisely pipetted, and injected into high performance liquid chromatograph for determination respectively. Results were shown in Table 3.

TABLE 3

Determination results of the content of ginsenoside Rg1

| Test sample | Content of ginsenoside Rg1 (mg/g or mg/ml) |
|---|---|
| Example 1 | 1.39 |
| Example 2 | 1.35 |
| Example 3 | 1.36 |
| Comparative Example 1 | 1.23 |
| Comparative Example 2 | 0.68 |
| Comparative Example 3 | 1.34 |

Conclusions: both the contents of ginsenoside of Examples 1-3 of the present invention and those of Comparative Example 1 and Comparative Example 3 are higher than that of Comparative Example 2, and the contents of Examples 1-3 and that of Comparative Example 3 are substantially the same, both higher than those of Comparative Examples 1 and 2. Therefore, from the extraction effect of ginsenoside ingredients represented by ginsenoside Rg1, it can be shown that the preparation methods of the present invention and Comparative Example 3 are more reasonable. Among them, the content of ginsenoside Rg1 in granules of Example 1 is the highest, and so Example 1 is a more preferred technical solution.

Effect Example 4 Research on Influence of Shenlingbaizhu Granules on Intestinal Mucosa Barrier in Juvenile Rat with Chronic Diarrhea Test Purposes Observe the influence of shenlingbaizhu preparations of Example 1 and Comparative Examples 1-3 on the intestinal mucosa barrier function in juvenile rats with chronic diarrhea.

Test Drugs

Shenlingbaizhu granules prepared in Example 1, Comparative Example 2 and Comparative Example 3, and shenlingbaizhu oral solution prepared in Comparative Example 1.

Method 4 weeks old Wistar rats were randomly divided into a blank control group, a natural recovery group (without drug treatment), glutamine group and Example 1 group (0.9 g/kg), Comparative Example 1 group (3 ml/kg), Comparative Example 2 group (1.8 g/kg) and control group 3 group (0.9 g/kg) (all the dosages were for rats by converting the equivalent clinical dosage of each preparation). Except for the blank control group and the natural recovery group, juvenile rats of other groups were given raw rhubarb decoction by gavage, thereby establishing the chronic diarrhea model. After successfully modeling, each juvenile rat from respective groups was given corresponding medicine 1 time a day by gavage, while each juvenile rat from the blank control group and the natural recovery group was given equal-volume sterile distilled water by gavage, for 2 weeks in total. After treatment, urine was collected to detect the ratio of lactulose to mannitol (L/M) in urine, and femoral artery blood was collected to detect plasma endotoxin.

Result: determination results of the lactulose/mannitol (L/M) ratio in urine and the plasma endotoxin of each group were respectively shown in Table 4 and Table 5.

The data in Table 4 and Table 5 showed that, the L/M ratio in urine and the plasma endotoxin level of juvenile rats in natural recovery group were significantly increased (P<0.01) after 2 weeks of administration, compared with the control group; and compared with the natural recovery group, the L/M ratio in urine and the plasma endotoxin level of juvenile rats in Example 1, Comparative Example 1, Comparative Example 2, Comparative Example 3 and glutamine groups are significantly decreased (P<0.05, P<0.01). However, the decrease of the L/M ratio in urine and the plasma endotoxin level of juvenile rats in Example 1 group were significantly larger than Comparative Example 1, Comparative Example 2 and Comparative Example 3 groups.

TABLE 4

Comparison of lactulose/mannitol ratio in urine of each group of juvenile rats ($\bar{x} \pm s$)

| Group | Number of animals | Dosage of administration | Urine volume (mL) | Lactulose/ mannitol (L/M) |
|---|---|---|---|---|
| Blank control group | 10 | — | 8.5 ± 1.4 | 0.20 ± 0.06 |
| Natural recovery group | 10 | — | 8.0 ± 1.8 | 0.29 ± 0.06** |
| Glutamine group | 10 | 6.0 g/kg | 8.3 ± 1.7 | 0.21 ± 0.05# |
| Example 1 | 10 | 0.9 g/kg | 8.0 ± 1.3 | 0.20 ± 0.04# |
| Comparative Example 1 | 10 | 3 ml/kg | 8.1 ± 1.2 | 0.23 ± 0.05# |
| Comparative Example 2 | 10 | 1.8 g/kg | 8.2 ± 1.6 | 0.25 ± 0.04 |
| Comparative Example 3 | 10 | 0.9 g/kg | 8.2 ± 1.4 | 0.24 ± 0.04 |

Compared with the blank control group, **$P < 0.01$; and compared with the natural recovery group, #$P < 0.05$.

TABLE 5

Comparison of plasma endotoxin level of each group of juvenile rats ($\bar{x} \pm s$)

| Group | Number of animals | Dosage of administration (g/kg) | Endotoxin (U/L) |
|---|---|---|---|
| Blank control group | 10 | — | 8.3 ± 1.7 |
| Natural recovery group | 10 | — | 14.4 ± 2.9** |
| Glutamine group | 10 | 6.0 | 11.4 ± 1.9# |
| Example 1 | 10 | 0.9 g/kg | 11.1 ± 1.7## |
| Comparative Example 1 | 10 | 3 ml/kg | 11.6 ± 1.8# |
| Comparative Example 2 | 10 | 1.8 g/kg | 12.9.0 ± 1.6 |

TABLE 5-continued

Comparison of plasma endotoxin level
of each group of juvenile rats ($\bar{x} \pm s$)

| Group | Number of animals | Dosage of administration (g/kg) | Endotoxin (U/L) |
|---|---|---|---|
| Comparative Example 3 | 10 | 0.9 g/kg | 11.5 ± 1.5[#] |

Compared with the blank control group, **P < 0.01; and compared with the natural recovery group, [#]P < 0.05, and [##]P <0.01.

Effect Example 5 (Clinical Observation Example) Observation and Comparison of Clinical Application of Shenlingbaizhu Granules of Example 1 and Comparative Example 3

Test Purposes

Investigate the efficacy and safety for children of shenlingbaizhu granules prepared by the present invention in the treatment of children's weakness of spleen and stomach through clinical verification.

1. Case Selection (1) 3-14 years old, irrespective of gender; (2) meet traditional Chinese medicine syndrome differentiation: weakness of spleen and stomach (loose stools or diarrhea, reduced appetite, abdominal distension after meal, fat and pale tongue body, or tooth marked tongue, thin and white tongue coating, thready and weak pulse); and/or meet western diagnostic criteria for chronic diarrhea (protracted diarrhea with a duration no less than half a month, or chronic diarrhea with a duration no less than 2 months; increased stool frequency no less than 3 times a day, accompanied with changes in stool volume and characters); (3) non-infectious diarrhea with a duration no less than half a month; (4) stool frequency no less than 3 times a day and no more than 7 times a day.

2. Test Method

A random-grouping and single-blind controlled test was performed.

Test group: 40 cases were given shenlingbaizhu granules prepared in Example 1 of the present invention: a 3-5 years old child was administered 3 times a day with 1 g per time; and a 5-14 years old child was administered 3 times a day with 2 g per time.

Control group: 40 cases were given shenlingbaizhu granules prepared in Comparative Example 3: a 3-5 years old child was administered 3 times a day with 1 g per time; and a 5-14 years old child was administered 3 times a day with 2 g per time.

Treatment course was 3 weeks.

3. Efficacy Evaluation Criteria

Clinically recovered: all symptoms of weakness of spleen and stomach were disappeared; and reference indicators of spleen and stomach were improved significantly.

Markedly effective: symptoms of weakness of spleen and stomach were significantly improved, and the improvement was no less than level 2; and reference indicators of spleen and stomach were improved.

Effective: symptoms of weakness of spleen and stomach were improved, and the improvement was no less than level 1; and objective indicators of cases were stable.

Invalid: symptoms of weakness of spleen and stomach and diagnostic indicators observed were not improved or aggravated.

2.1.4 Experimental Results

The overall effective rate was 100% and the cure rate was 82.5% in the test group, while the overall effective rate was 90% and the cure rate was 65% in the control group. Although there was no significance between the two groups (p>0.05), as to the improvement in stool frequency, the test group was superior to the control group; results were shown in Table 6. In addition, the experimental group was also superior to the control group in the compliance and convenience for taking medicine.

TABLE 6

Results of clinical observation

| Group | Stool frequency before treatment | Stool frequency after treatment | Numbers of people with stool abnormality before treatment | Numbers of people with stool abnormality after treatment |
|---|---|---|---|---|
| Test Group | 6.8 times/day on average | 1.4 times/day on average | 40 | 5 |
| Control Group | 6.6 times/day on average | 1.8 times/day on average | 40 | 8 |

None of the 40 cases of children in the test group was found to have any adverse reactions and hepatic and renal dysfunction, indicating that the granules of the present application have good safety.

In summary, the above clinical tests have proved that the shenlingbaizhu granules prepared by the preparation method of the present invention have certain advantages in the treatment of children suffering from weakness of spleen and stomach compared to those in Comparative Example 3, and further, the granules have a good safety, suitable for children.

The description of specific embodiments of the present invention is not intended to limit the present invention, and various changes or modifications can be made by those skilled in the art in light of the present invention, and should fall within the scope of the appended claims of the present invention as long as they do not depart from the spirit of the present invention.

The invention claimed is:

1. Shenlingbaizhu granules comprising an extract of raw material medicines and excipients, wherein the raw material medicines include 400 parts by weight of *Radix ginseng,* 400 parts by weight of *Poria,* 400 parts by weight of stir-baked *Rhizoma atractyldis macrocephalae* in bran, 400 parts by weight of *Rhizoma dioscoreae,* 300 parts by weight of stir-fried *Semen dolichoris album,* 200 parts by weight of *Semen nelumbinis,* 200 parts by weight of stir-baked *Semen coicis* in bran, 200 parts by weight of *Fructus amomi villosi,* 200 parts by weight of *Radix platycodonis* and 400 parts by weight of *Radix glycyrrhizae,* and the excipients include citric acid, stevioside and lactose; and wherein a clear solution can be obtained after dispersion by adding a proper amount of water into the shenlingbaizhu granules.

2. The shenlingbaizhu granules according to claim 1, wherein the shenlingbaizhu granules are administered to a 3-5 years old child in need 3 times a day with 1 g per time; and are administered to a 5-14 years old child in need 3 times a day with 2 g per time.

3. An administration method of the shenlingbaizhu granules according to claim 1, including administering the shenlingbaizhu granules to a child suffering from weakness of spleen and stomach, anorexia and loose stools, short breath and cough, and/or limb tiredness and hypodynamia, wherein a 3-5 years old child is administered 3 times a day with 1 g per time, and a 5-14 years old child is administered 3 times a day with 2 g per time.

4. A method for treating a child suffering from weakness of spleen and stomach, anorexia and loose stools, short breath and cough, and/or limb tiredness and hypodynamia, comprising administrating the shenlingbaizhu granules according to claim 1 to the child.

5. A preparation method of shenlingbaizhu granules which raw material medicines include:
400 parts by weight of *Radix ginseng*, 400 parts by weight of *Poria*, 400 parts by weight of stir-baked *Rhizoma atractyldis macrocephalae* in bran, 400 parts by weight of *Rhizoma dioscoreae*, 300 parts by weight of stir-fried *Semen dolichoris album*, 200 parts by weight of *Semen nelumbinis*, 200 parts by weight of stir-baked *Semen coicis* in bran, 200 parts by weight of *Fructus amomi villosi*, 200 parts by weight of *Radix platycodonis* and 400 parts by weight of *Radix glycyrrhizae*;
wherein the preparation method includes following steps:
(1) preparing the raw material medicines as above;
(2) extracting the *Fructus amomi villosi* using steam distillation method to obtain *Fructus amomi villosi* volatile oil, collecting aqueous solution obtained upon distillation in another container, and reserving residues for later use;
(3) adding 80-95% ethanol into the residues obtained from step (2) with the *Radix ginseng*, the *Rhizoma atractyldis macrocephalae*, and the *Radix platycodonis* and soaking in the ethanol for 24 hours, the volume of the ethanol being 8-12 times the weight of the materials to be soaked, heating under reflux for 2-3 hours, filtering, and after recovery of ethanol, concentrating the filtrate to obtain a clear paste with a relative density of 1.10-1.20 at 65° C.; and further, adding 30-60% ethanol into the filter residues and refluxing the filter residues in the ethanol for 2-3 hours, the volume of the ethanol being 8-10 times the weight of the filter residues to be refluxed, filtering, and after recovery of ethanol, concentrating the filtrate to obtain a clear paste with a relative density of 1.10-1.20 at 80° C., and reserving the filter residues for later use;
(4) adding water into the filter residues obtained from step (3) with the *Poria*, the *Rhizoma dioscoreae*, the stir-fried *Semen dolichoris album*, the *Semen nelumbinis*, the stir-baked *Semen coicis* in bran and the *Radix glycyrrhizae* and decocting in the water for two times with 1-3 hours for the first time and 1-2 hours for the second time, the volume of water added per time being 8-12 times the weight of the materials to be decocted, combining the decoctions, filtering, and combining the filtrate with the aqueous solution obtained from step (2), allowing to stand, filtering, and concentrating the filtrate until its relative density is 1.15-1.30 at 80° C., and then adding therein the two clear pastes obtained from step (3), followed by further concentrating to obtain a clear paste with a relative density of 1.10-1.25 at 80° C., and spray-drying the clear paste to obtain spray-dried powders;
(5) adding into the spray-dried powders obtained from step (4) 0.5-1% of citric acid and 0.01-0.05% of stevioside based on the weight of the spray-dried powders, as well as a proper amount of lactose, uniformly mixing, and granulating the mixture by dry granulation method, spraying therein the *Fructus amomi villosi* volatile oil obtained from step (2), uniformly mixing, and preparing the mixture into 1000 parts by weight of granules; and
(6) subpackaging the granules obtained from step (5) with 1 g per bag.

6. The preparation method according to claim 5, wherein step (2) further comprises, before extracting the *Fructus amomi villosi* to obtain the *Fructus amomi villosi* volatile oil, adding water into the *Fructus amomi villosi* and soaking in the water for 1 hour, the water added being 8-12 times the weight of the *Fructus amomi villosi*.

7. The preparation method according to claim 5, wherein step (2) further comprises, before extracting the *Fructus amomi villosi* to obtain the *Fructus amomi villosi* volatile oil, adding water into the *Fructus amomi villosi* and soaking in the water for 1 hour, the water added being 10 times the weight of the *Fructus amomi villosi*.

8. The preparation method according to claim 5, wherein the *Fructus amomi villosi* is extracted using steam distillation method for 4-8 hours, thereby obtaining the *Fructus amomi villosi* volatile oil.

9. The preparation method according to claim 8, wherein the *Fructus amomi villost* is extracted using steam distillation method for 6 hours, thereby obtaining the *Fructus amomi villost* volatile oil.

10. The preparation method according to claim 5, wherein in step (3), the residues obtained from step (2) with the *Radix ginseng*, the *Rhizoma atractyldis macrocephalae* and the *Radix platycodonis* are extracted in 95% ethanol, and further, the filter residues are extracted in 50% ethanol.

11. The preparation method according to claim 10, wherein in step (3), the volume of 95% ethanol is 8-10 times the weight of the materials, and the volume of the 50% ethanol is 8 times the weight of the filter residues.

12. Shenlingbaizhu granules prepared by the preparation method according to claim 5, wherein a clear solution can be obtained after dispersion by adding a proper amount of water into the shenlingbaizhu granules.

13. A preparation method of shenlingbaizhu granules which raw material medicines include:
400 parts by weight of *Radix ginseng*, 400 parts by weight of *Poria*, 400 parts by weight of stir-baked *Rhizoma atractyldis macrocephalae* in bran, 400 parts by weight of *Rhizoma dioscoreae*, 300 parts by weight of stir-fried *Semen dolichoris album*, 200 parts by weight of *Semen nelumbinis*, 200 parts by weight of stir-baked *Semen coicis* in bran, 200 parts by weight of *Fructus amomi villosi*, 200 parts by weight of *Radix platycodonis* and 400 parts by weight of *Radix glycyrrhizae*;
wherein the preparation method includes following steps:
(1) preparing the raw material medicines as above;
(2) adding water into the *Fructus amomi villost* and soaking in the water for 1 hour, the water added being 10 times the weight of the *Fructus amomi villost*, extracting the *Fructus amomi villost* using steam distillation method for 6 hours, and collecting *Fructus amomi villost* volatile oil for later use; collecting aqueous solution obtained upon distillation in another container for later use; and reserving residues for later use;
(3) adding 95% ethanol into the residues obtained from step (2) with the *Radix ginseng*, the *Rhizoma atractyldis macrocephalae* and the *Radix platycodonis* and soaking in the ethanol for 24 hours, the volume of the 95% ethanol being 8-10 times the weight of the materials to be soaked, heating under reflux for 3 hours, filtering, and after recovery of ethanol, concentrating the filtrate to obtain a clear paste with a relative density of 1.10-1.20 at 65° C.; and further, adding 50% ethanol into the filter residues and refluxing the filter residues in the ethanol for 3 hours, the volume of the 50% ethanol being 8 times the weight of the filter residues to be refluxed, filtering, and after recovery of ethanol, concentrating the filtrate to obtain a clear paste with a relative density of 1.10-1.20 at 80° C., and reserving the filter residues for later use;

(4) adding water into the filter residues obtained from step (3) with the *Poria*, the *Rhizoma dioscoreae*, the stir-fried *Semen dolichoris album*, the *Semen nelumbinis*, the stir-baked *Semen coicis* in bran and the *Radix glycyrrhizae* and decocting in the water for two times with 2 hours for the first time and 1.5 hours for the second time, the volume of water added per time being 10 times the weight of the materials to be decocted, combining the decoctions, filtering, and combining the filtrate with the aqueous solution obtained from step (2), allowing to stand, filtering, and concentrating the filtrate until its relative density is 1.15-1.30 at 80° C., and then adding therein the two clear pastes obtained from step (3), followed by further concentrating to obtain a clear paste with a relative density of 1.15-1.20 at 80° C., and spray-drying the clear paste to obtain spray-dried powders;

(5) adding into the spray-dried powders obtained from step (4) 1% of citric acid and 0.01-0.05% of stevioside for the weight of the spray-dried powders, as well as a proper amount of lactose, uniformly mixing, and granulating the mixture by dry granulation method, spraying therein the *Fructus Amomi villosi* volatile oil obtained from step (2), uniformly mixing, and preparing the mixture into 1000 parts by weight of granules; and (6) subpackaging the granules obtained from step (5) with 1 g per bag.

14. Shenlingbaizhu granules prepared by the preparation method according to claim 13, wherein a clear solution can be obtained after dispersion by adding a proper amount of water into the shenlingbaizhu granules.

* * * * *